United States Patent [19]
Minami

[11] Patent Number: 5,905,595
[45] Date of Patent: May 18, 1999

[54] SURFACE INSPECTION METHOD, SURFACE INSPECTION APPARATUS, AND PRISM

[75] Inventor: Hideaki Minami, Hirakata, Japan

[73] Assignee: Tsubakimoto Chain Co., Osaka, Japan

[21] Appl. No.: 08/786,485

[22] Filed: Jan. 21, 1997

[30] Foreign Application Priority Data

Jan. 23, 1996 [JP] Japan .................................. 8-009373

[51] Int. Cl.$^6$ .......................... G02B 27/10; G02B 27/14; G02N 21/06
[52] U.S. Cl. ..................... 359/618; 356/241.1; 359/629
[58] Field of Search .................... 359/625, 629, 359/833, 834, 618; 356/241.1–241.5

[56] References Cited

U.S. PATENT DOCUMENTS

| | | | |
|---|---|---|---|
| 3,073,210 | 1/1963 | Packard | 40/542 |
| 4,072,427 | 2/1978 | Alsberg | 356/241 |
| 4,297,032 | 10/1981 | Temple | 356/366 |
| 4,963,018 | 10/1990 | West | 356/1 |
| 5,126,872 | 6/1992 | Birkle | 359/196 |
| 5,298,989 | 3/1994 | Tsukahara et al. | 348/126 |
| 5,661,294 | 8/1997 | Buchmann et al. | 250/233 B |
| 5,719,677 | 2/1998 | Guerra | 356/375 |

FOREIGN PATENT DOCUMENTS 8-29146  2/1996  Japan .

*Primary Examiner*—Georgia Epps
*Assistant Examiner*—Ricky Mack
*Attorney, Agent, or Firm*—Darby & Darby

[57] ABSTRACT

A method for inspecting the surface of an inspection object with a picked-up image obtained by entering light from the inspection object into an annular prism, and picking-up the light emitted from the prism, and an apparatus used for execution thereof. Also a prism composed of a columnar light permeable material, having a space of a circular truncated cone or a truncated pyramid opened at both axial end sides in its inside, to be used in this apparatus.

16 Claims, 10 Drawing Sheets

SURFACE INSPECTION METHOD, SURFACE INSPECTION APPARATUS, AND PRISM

BACKGROUND OF THE INVENTION

The present invention relates to a surface inspection method, surface inspection apparatus, and prism for inspecting the surface of an object of inspection.

When manufacturing small pieces such as short columnar or cylindrical parts, inspections are performed for performed for the presence of defects such as flaw, stain and uneven color on the inner and outer surface of the small pieces, and the defect rate of small pieces is lowered. In such inspection of the inner and outer surface, small pieces to be inspected are supported by proper means, rotated about the axial center, and the surface of the rotating small pieces is inspected visually or by camera, and the quality of surfaces of small pieces is evaluated on the basis of the visual or photographic results.

In such conventional inspection method, however, the small pieces to be inspected must be rotated, and a rotating mechanism is needed, which increases the inspection cost. Besides, since the small pieces must be rotated at least one revolution, the inspection time is longer, or some pieces may elude inspection if a slip occurs in rotation. Moreover, to inspect the surface of small pieces, a mechanism for conveying small pieces is needed, which also adds to the cost, and increases inspection time.

BRIEF SUMMARY OF THE INVENTION

The invention has been devised to solve the above problems, and it is a primary object of the invention to present a surface inspection method, surface inspection apparatus, and prism for inspecting the surface of an object of inspection at high speed and at low cost.

In the surface inspection method and apparatus of the invention, light from an object of inspection is put into an annular prism, and light emitted from the prism is picked up, and the surface of the inspection object is inspected from the obtained image.

The light from the object of inspection enters the inner circumferential face of the prism, is reflected by the outer circumferential face of the prism, is projected on the inner circumferential face, and totally reflected by the inner circumferential face. The totally reflected light is emitted from the shaft end plane of the prism, and this light enters pick-up means, and the surface of the inspection object is inspected in the image picked-up by the pick-up means.

As a result, an image developed in an annular form is obtained without rotating the inspection object, and, for example, approval or rejection of the surface of the inspection object can be determined instantly.

The invention may be also composed by having a penetration hole through which the inspection object passes and a reflector for projecting the light emitted from the prism, so that the image projected on the reflector may be taken. Hence, the image can be picked-up without disturbing passing of the inspection object.

When the prism and reflector are disposed in the vertical direction, for example, inspection objects are dropped and inspected one by one, or inspection objects conveyed in the lateral direction can be inspected sequentially. Or by disposing them in the lateral direction, pop out inspection of objects may be carried out by making use of an air chute or other means.

In the above apparatus may also comprise a light source for emitting light to the surface of the inspection object and light emission control means for controlling light emission of the light source when the inspection object gets into the picking-up field of the pick-up means, and the image displayed in the reflector may be taken when the light source emits light. The prism has an opening of a circular truncated cone with one side larger in diameter than the other side, and the light entering from the opening is reflected by the surrounding surface, and is emitted from the axial end of the other side.

In this embodiment, the light from the inspection object enters the inner circumferential face of the prism, and is reflected by the outer circumferential face of the prism, and is projected on the inner circumferential face and totally reflected by the inner circumferential face. The totally reflected light is emitted from the axial end of the prism, and the light is projected on the reflector, and the surface of the inspection object is displayed on the reflector. On the basis of the image obtained by picking-up the image displayed on the reflector, the outside or inside surface of the inspection object which is a columnar or cylindrical body may be inspected. Thus, without rotating the inspection object, approval or rejection of the surface of the inspection object can be instantly determined, for example.

Furthermore, a ring-shaped lens may be disposed at the exit side of the prism light. As a result, the light emitted from the prism passes through the ring-shaped lens, and an image magnifying the surface of the inspection object is displayed on the reflector. Therefore, the surface of the inspection object can be inspected at high precision.

The prism of the invention has a space shaped like a circular truncated cone opened at the both axial ends of a column, inside of a column composed of light permeable material. When light enters the inner circumferential face forming the space of circular truncated cone provided in the prism, the light is reflected by the outer circumferential face of the prism, and is totally reflected by the inner circumference face, and then is emitted in an annular state from the axial end of the prism. Therefore, when the light from the columnar body or cylindrical body is put into the prism, the image corresponding to developing the surface of the columnar body or cylindrical body into an annular form can be displayed. When using such prism of the invention, not only the light from the surface normal to the axis of the annular prism but also the light from the parallel plane can be emitted from the axial end surface normal to the axis.

The outer circumferential face of the annular prism may be orthogonal to the axial end surface or may be oblique. Or when the space of the circular truncated cone is replaced by a space of a prismoid, it may be applied to a polygonal column or polygonal cylinder.

The above and further objects and features of the invention will more fully be apparent from the following detailed description with accompanying drawings.

DETAILED DESCRIPTION OF THE INVENTION

Figure 1:
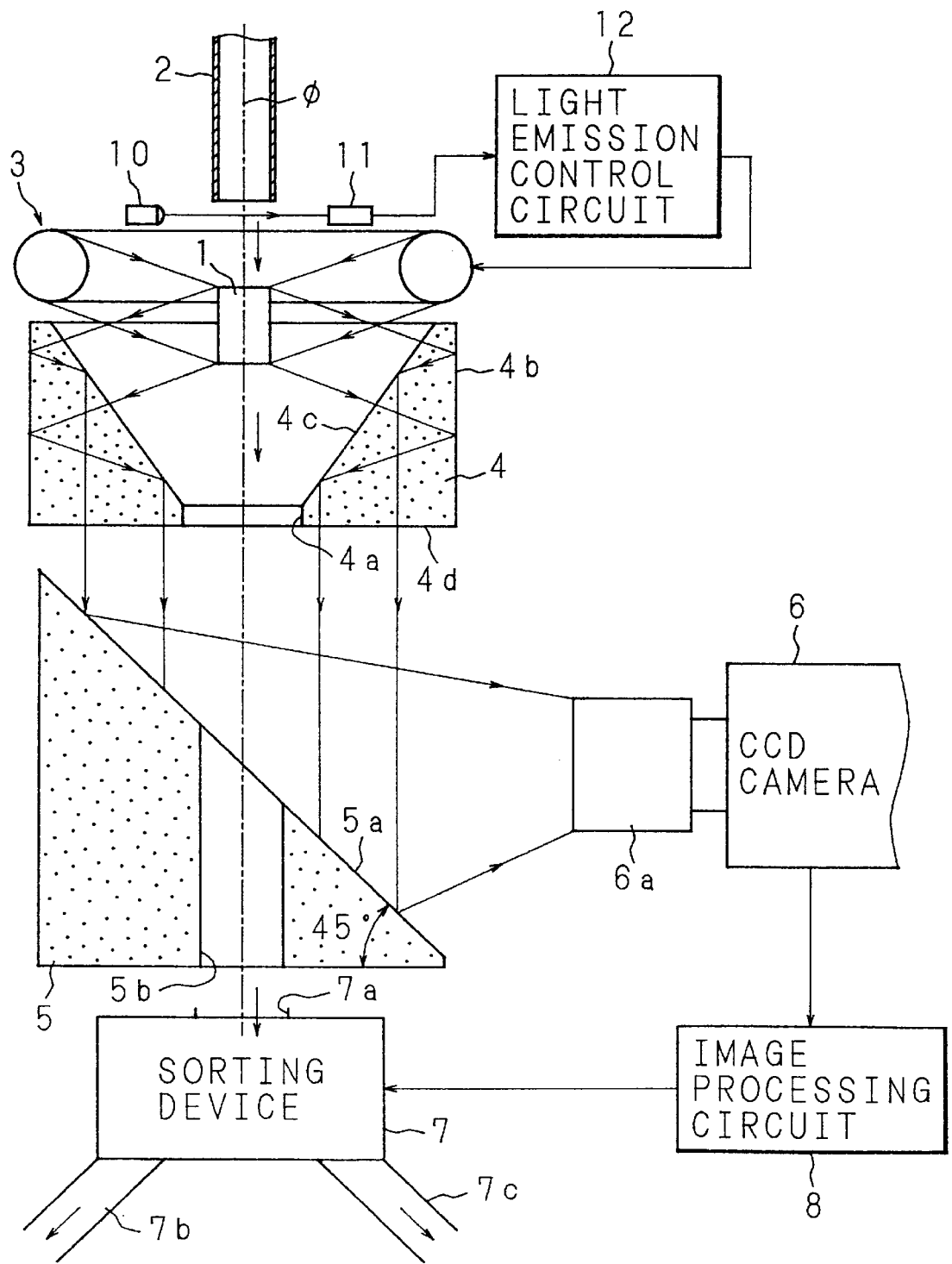
FIG. 1 is a schematic configuration diagram showing an embodiment 1 of a surface inspection apparatus of the invention together with an inspection object.

Referring now to the drawings, embodiments of the invention are described in detail below.

[Embodiment 1]

FIG. 1 is a schematic configuration diagram showing embodiment 1 of a surface inspection apparatus of the invention together with an inspection object.

A guide tube 2 of a proper length for guiding the fall of an inspection object 1 is of a short columnar or cylindrical form and is disposed vertically. Beneath the guide tube 2, an annular light source 3 being a multiplicity of LEDs (light emitting diodes) arranged circumferentially is disposed. Beneath the light source 3, an annular cone prism 4 is disposed. Inside the cone prism 4, a space of a circular truncated cone larger in diameter at the top is formed, and the outer circumferential face 4b of the cone prism 4 is mirror-finished in order to reflect the light. The bottom 4d and outer circumference face 4b of the cone prism 4 are orthogonal to each other, and the inner circumference face 4c forming the circular truncated cone space is at an inclination angle of about 50° to the bottom 4d.

Beneath the cone prism 4, a reflector 5 of a triangular columnar form having the reflection surface 5a inclined obliquely upward at an angle of 45° is disposed. In the middle of the reflection surface 5a a penetration hole 5b of a slightly smaller diameter than the opening 4a is formed in the bottom 4d. To the side of the reflector 5 at the side of the reflector 5 confronting the reflection surface 5a, a high sensitivity CCD (charge coupled device) camera 6 is disposed with the photo receptor side of the lens 6a directed to the side of the reflection surface 5a and the optical axis of the lens 6a at an angle of 45° to the reflection surface 5a. Beneath the reflector 5, a storing device 7 is disposed with an inspection object fall hole 7a opposite to the penetration hole 5b of the reflector 5. This sorting device 7 is designed to sort the inspection object falling into the inspection object fall hole 7a by an air drive mechanism, and the inspection object sorted to be defective is discharged into a defective outlet 7b, and the inspection object sorted to be conforming is discharged into a conforming outlet 7c. The image data issued by the CCD camera 6 is put into an image processing circuit 8.

The image processing circuit 8 is designed to store a reference image data representing an inspection object 1 which is free from flaw or stain. By reading out the reference image data, the image data entered from the CCD camera 6 and the read-out reference image data may be compared. As a result the comparison, when the difference is large, that is, when the object is judged to be defective due to a flaw or stain on the surface of the inspection object, the sorting device 7 is driven, and the inspection object falling into the inspection object fall hole 7a is discharged at the defective outlet 7b by the air drive mechanism, or when judged to be conforming, it is discharged at the conforming outlet 7c.

The centers of the guide tube 2, light source 3, cone prism 4, penetration hole 5b of reflector 5, and opening 7a of sorting device 7 are aligned on an optical central axis $\phi$. Between the guide tube 2 and light source 3, a light emitting diode 10 and a photo receptor transistor 11 are opposite to each other across the optical central axis $\phi$, and the light emitted from the light emitting diode 10 is received by the photo receptor transistor 11. The received signal of the photo receptor transistor 11 is put into a light emission control circuit 12. The light emission control circuit 12 is designed to issue a light emission control signal when the received signal is cut off. The light emission control signal of the light emission control circuit 12 is applied to the light source 3, and when the light emission control signal is given, the light source 3 emits light instantly. The height position of the light emitting diode 10 and control operation of the light emission control circuit 12 are defined so that the timing of emission of light by the light source 3 may coincide with the entry of the inspection object 1 into the picking-up field of the CCD camera 6.

Next is explained the method of inspecting the surface of inspection object by using thus constituted surface inspection apparatus. First, the light emitting diode 10 is left to emit light, and the CCD camera 6 is in ready state. When the inspection object 1 is supplied into the upper end opening of the guide tube 2, the inspection object 1 is guided by the guide tube 2, and falls with the axial direction of the inspection object 1 being in the vertical direction. When the inspection object 1 gets out of the lower end opening of the guide tube 2, the light emitted from the light emitting diode 10 is shielded, and the receiving output of the photo receptor transistor 11 is eliminated instantly. As a result, the light emission control circuit 12 issues the light emission control signal to supply to the light source 3, and the light source 3 emits light instantly. Accordingly, the light is emitted to the surface of the inspection object 1 immediately before falling into the cone prism 4. The emitted light is reflected by the surface of the inspection object 1, and the reflected light enters the cone prism 4, and is reflected by the outer circumference face 4b. This reflected light is totally reflected on the inclined inner circumference face 4c formed inside of the cone prism 4. The totally reflected light is projected to the reflector 5 parallel to the optical central axis $\phi$ from the cone prism 4, is reflected by the reflection surface 5a, is diffracted by 90° to the optical central axis $\phi$, and then enters the lens 6a of the CCD camera 6.

Figure 2:
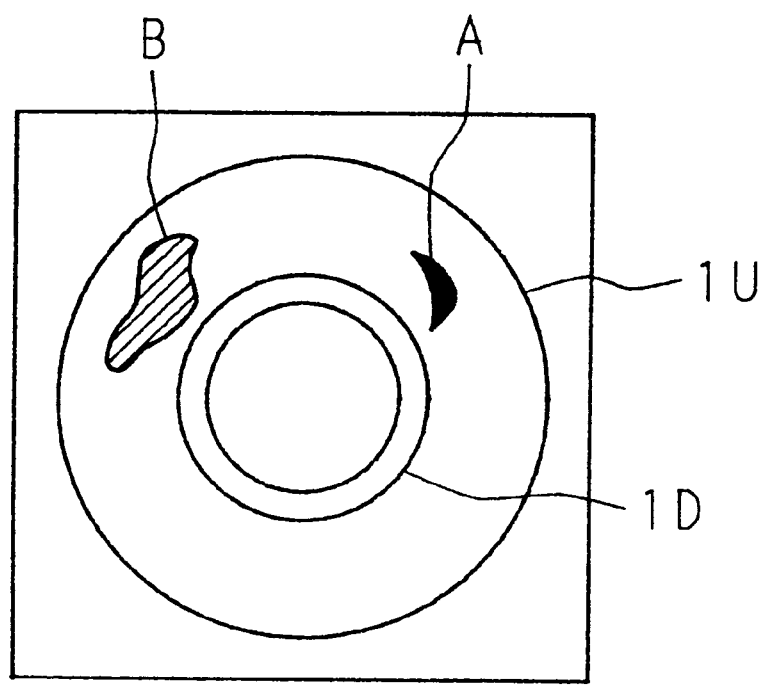
FIG. 2 is a diagram showing a picked-up image.

In this way, when the light reflected on the surface of the inspection object 1 is reflected by the outer circumference face 4b of the cone prism 4, and is totally reflected by the inner circumference face 4c, the outer circumference face of the inspection object 1 is developed in an annular form, and the outer circumference face of the inspection object 1 is displayed in an annular form on the reflection surface 5a of the reflector 5 as shown in FIG. 2. Incidentally, 1U denotes the upper end position of the inspection object 1, and 1D shows the lower end position, showing the state of presence of flaw A and stain B.

The CCD camera 6 instantly picks up the surface of the inspection object 1 when the light source 3 emits light. Accordingly, if there is any flaw or stain on the surface of the inspection object 1, the flaw A and stain B shown in FIG. 2 are taken by the CCD camera 6. The image data of the picture taken thus by the CCD camera 6 is put into the image processing circuit 8. The image processing circuit 8 reads out the reference image data of the inspection object 1 free from flaw A or stain B on the surface being taken and stored preliminarily in the memory, and compares the read-out reference image data and the image data entered from the CCD camera 6. When the presence of flaw A and stain B is recognized as a result of comparison, the image processing circuit 8 issues a sorting drive signal to drive the sorting device 7.

As a result, the sorting device 7 sorts so as to discharge the inspection object 1 falling in the inspection object fall hole 7*a* at the defective outlet 7*b*. Therefore, the inspection object 1 of which surface is picked up by the CCD camera 6 passes through the cone prism 4, further passes through the penetration hole 5*b* of the reflector 5, falls into the inspection object fall hole 7*a*, and then is discharged at the defective outlet 7*b*.

On the other hand, when the CCD camera 6 takes the inspection object 1 free from flaw A and stain B, there is no difference between the image data put into the image processing circuit 8 from the CCD camera 6 and the reference image data read out from the memory, and the image processing circuit 8 does not issue the sort drive signal for driving the sorting device 7. Accordingly, the sorting device 7 sorts so as to discharge the inspection object 1 falling in the inspection object fall hole 7*a* at the conforming outlet 7*c*. In this way, without rotating the inspection object 1, its outer circumference face can be taken, and the surface of the inspection object can be inspected instantly. Besides, it does not require any mechanism for positioning and rotating the inspection object, and the surface can be inspected at low cost with the inspection efficiency improved outstandingly. Still more, capable of inspecting the inspection object without making contact, the inspection object is not flawed or stained by inspection.

Figure 3:
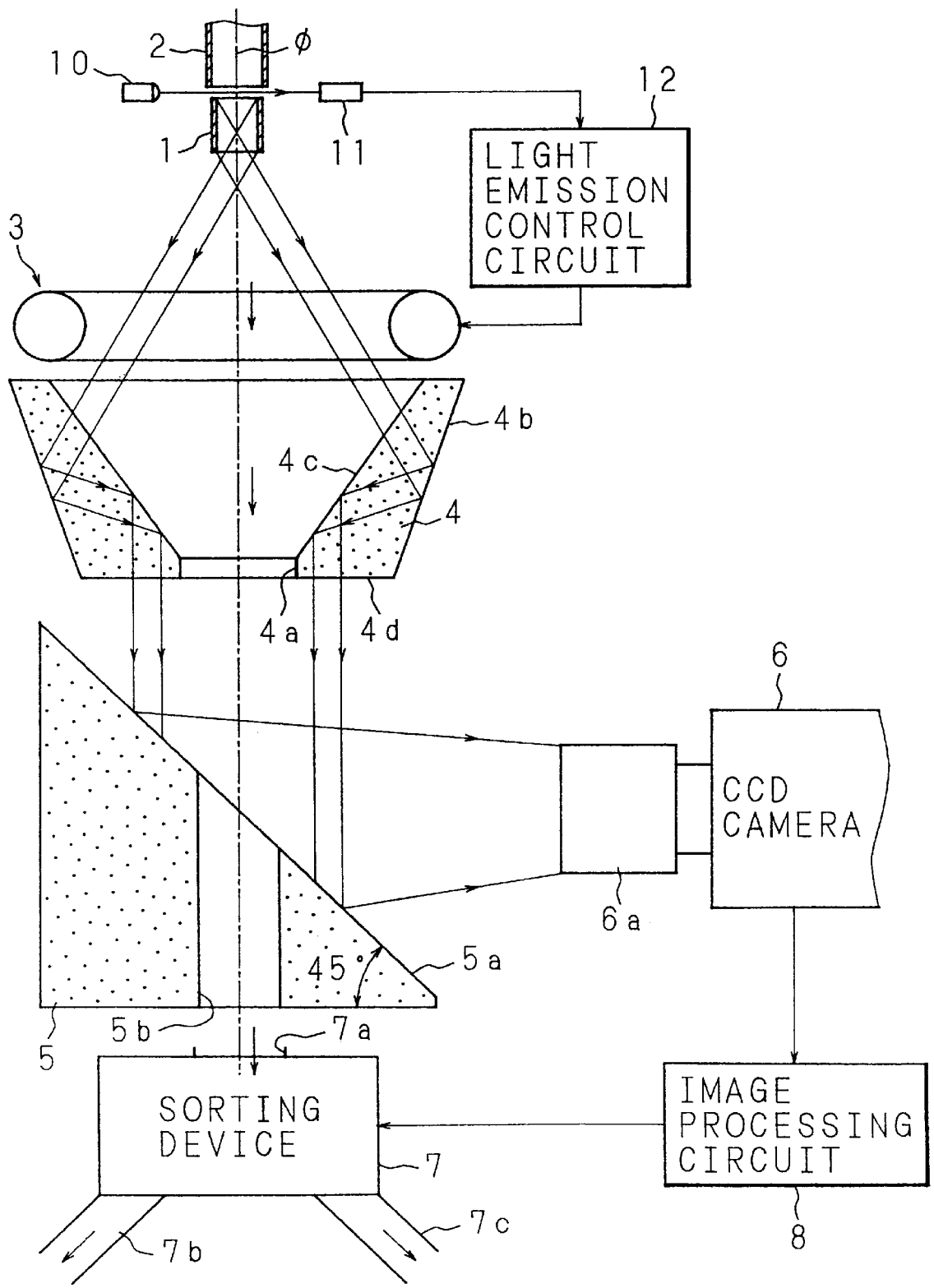
FIG. 3 is a schematic configuration diagram showing embodiment 1 of the surface inspection apparatus of the invention together with a different inspection object.

FIG. 3 is a schematic configuration diagram of a surface inspection apparatus, showing the state of inspection of inside surface of a cylindrical inspection object by the surface inspection apparatus of the invention, together with an inspection object.

A cone prism 4 is expanded in diameter form the lower end side toward the upper end side, a space of a circular truncated cone is formed inside thereof, and the lower end of the space communicates with an opening 4*a*, thereby forming a shape of a tube tapered with a specific thickness. The slope angle of an inner circumference face 4*c* forming the space of circular truncated cone is selected smaller than the slope angle of an outer circumference face 4*b*, and the thickness of the lower end side is selected greater than the thickness of the upper end side. The outer circumference face 4*b* is mirror-finished. The distance between the lower end of a guide tube 2 and a light source 3 is selected longer than in the case of the surface inspection apparatus shown in FIG. 1. The constitution of other than the cone prism 4 is same as in the constitution shown in FIG. 1, and same components are identified with same reference numerals.

Using thus constituted surface inspection apparatus, the method of inspecting the inside surface of the inspecting object is described below.

When the cylindrical inspection object 1 is supplied to the upper end of the guide tube 2, the inspection object 1 is guided by the guide tube 2, and falls in the axial direction of the inspection object 1 in the vertical direction. When the inspection object 1 comes out of the lower end opening of the guide tube 2, the light emitted from the light emitting diode 10 is cut off, and the receiving output of the photo receptor transistor 11 is eliminated instantly. As a result, the light emission control circuit 12 issues a light emission control signal to supply to the light source 3, thus the light source 3 emits light instantly. Consequently, light is emitted to the inside surface of the inspection object 1 immediately before falling into the cone prism 4. The emitted light is reflected by the inside surface of the inspection object 1, and the reflected light is entered in the cone prism 4 and then reflected by the outer circumference face 4*b* of the cone prism 4. The reflected light is totally reflected by the inclined inner circumference face 4*c* forming the circular truncated cone of the cone prism 4.

Figure 4:
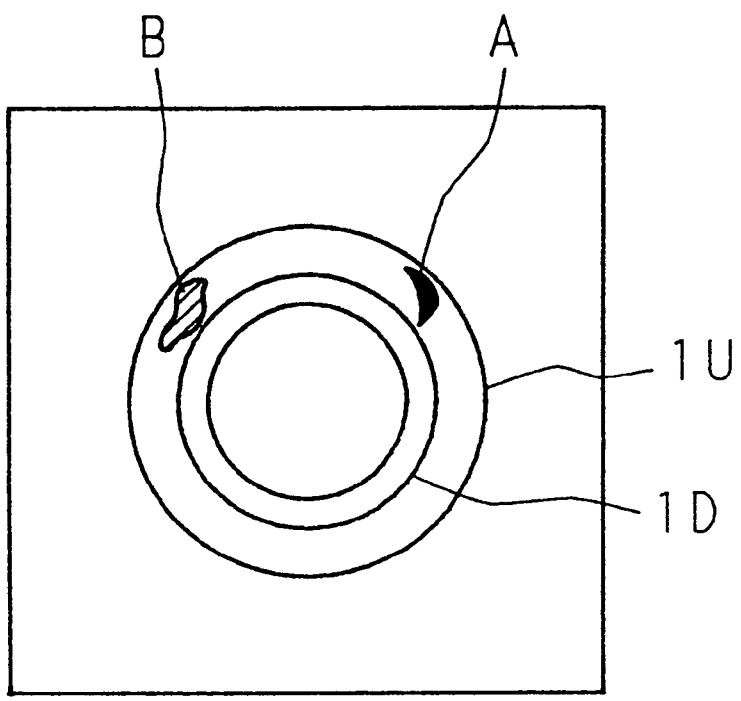
FIG. 4 is a diagram showing a picked-up image.

The totally reflected light is projected and reflected by the reflection surface 5*a* of the reflector 5 parallel to an optical central axis φ from the cone prism 4, is diffracted by 90° to the optical central axis φ, and entered the lens 6*a* of the CCD camera 6. In this way, the light reflected by the inside surface of the inspection object 1 is reflected by the outer circumference face of the cone prism 4, and is totally reflected by the inner circumference face, whereby the inner circumference face of the inspection object 1 is developed in an annular form, and the inside surface of the inspection object 1 is annularly displayed on the reflection surface 5*a* of the reflector 5 as shown in FIG. 4. In FIG. 4, 1U indicates the upper end position of the inspection object 1, and 1D shows the lower end position, showing the presence of flaw A and stain B.

The CCD camera 6 takes the inside surface of the inspection object 1 when the light source 3 instantly emits light. Accordingly, if there is any flaw A or stain B on the inside surface of the inspection object 1, the flaw A and stain B shown in FIG. 4 are taken by the CCD camera 6. The image data of the picture taken thus by the CCD camera 6 is put into the image processing circuit 8. The image processing circuit 8 reads out the reference image data stored preliminarily in the memory, and compares the read-out reference image data and the image data entered from the CCD camera 6. When presence of flaw A and stain B is recognized as a result of comparison, the image processing circuit 8 issues a sorting drive signal to drive the sorting device 7.

As a result, the sorting device 7 sorts so as to discharge the inspection object 1 falling in the inspection object fall hole 7*a* at the defective outlet 7*b*. Therefore, the inspection object 1 of which surface is taken by the CCD camera 6 passes through the cone prism 4, further passes through the penetration hole 5*b* of the reflector 5 falls into the inspection object fall hole 7*a*, and then comes out through the defective outlet 7*b*. On the other hand, when the CCD camera 6 takes the inspection object 1 free from flaw A and stain B, there is no difference between the image data put into the image processing circuit 8 from the CCD camera and the reference image data read out from the memory, and the image processing circuit 8 does not issue the sort drive signal for driving the sorting device 7. Accordingly, the sorting device 7 sorts so as to discharge the inspection object 1 falling in the inspection object fall hole 7*a* at the conforming outlet 7*c*.

In this way, without rotating the inspection object 1, the inside surface of the inspection object 1 can be taken, and the surface of the inspection object 1 can be inspected instantly. Besides, it does not require any mechanism for positioning and rotating the inspection object 1, so that the surface can be inspected at low cost, and the inspection efficiency is improved outstandingly. Still more, capable of inspecting the inspection object 1 without making contact, the inspection object 1 is not flawed or stained by inspection.

[Embodiment 2]

Figure 5:
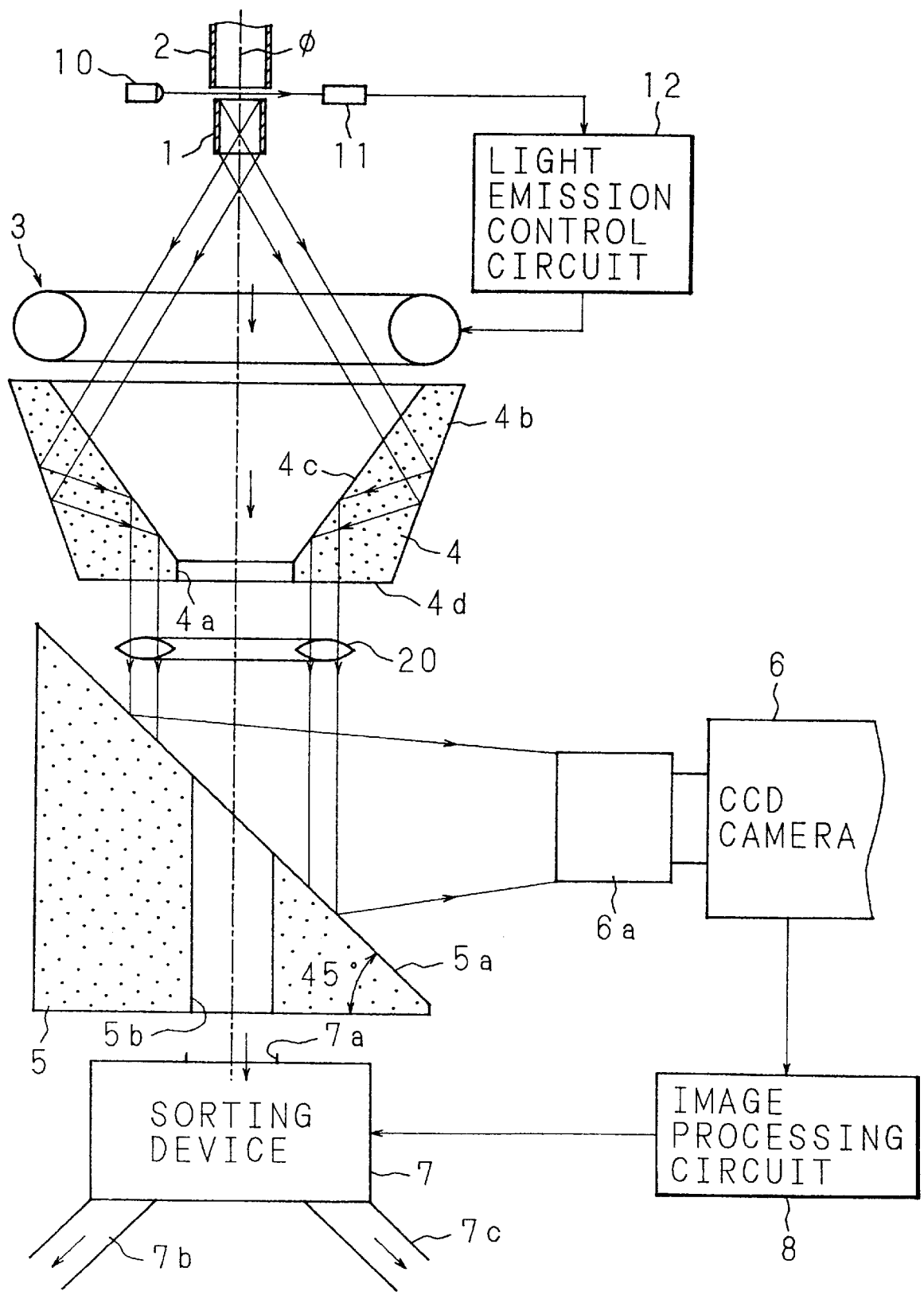
FIG. 5 is a schematic configuration diagram showing embodiment 2 of a surface inspection apparatus of the invention together with an inspection object.

FIG. 5 is a schematic configuration diagram showing another surface inspection apparatus for inspecting the inside surface of a cylindrical inspection object together with the inspection object.

At a lower position properly remote from the lower end of a cone prism 4, a ring-shaped convex lens 20 of a slightly larger inside diameter than the inside diameter of the cone prism 4 at the lower end side is disposed with its diameter direction orthogonal to an optical central axis φ. The other constitution is same as the surface inspection apparatus shown in FIG. 3, and same reference numeral are given to same constituent members. The ring-shaped convex lens 20 can be composed by disposing a plurality of sector-shaped cylindrical lenses annularly.

A method of inspecting the inside surface of an inspection object by using this surface inspection apparatus is described below. The inspection object 1 is supplied and dropped in the guide tube 2, the light source 3 emits light in the midst of falling, and the image of the inside surface of the inspection object 1 projected on the reflection surface 5a is taken by the CCD camera 6, whereby surface of the inspection object 1 is inspected, same as the embodiment shown in FIG. 3.

Herein, however, the light reflected by the inside surface of the inspection object 1 passes through the ring-shaped convex lens 20 on the way where it is totally reflected by the cone prism 4 and projected on the reflector 5. As a result, on the reflection surface 5a of the reflector 5, the inside surface of the inspection object 1 is developed in an annular form, and the inside surface of the inspection object 1 magnified by the ring-shaped convex lens 20 is displayed in an annular form. Therefore, if there is any flaw or stain on the inside surface of the inspection object 1, it can be displayed in magnification, and the precision of inspection can be enhanced.

Incidentally, since the reflected light of the inside surface of the inspection object 1 is displayed annularly on the reflection surface 5a as the inside surface is developed inward, the size of flaw or stain is reduced. But since it is magnified by the ring-shaped convex lens 20, it is possible to inspect in the same condition as when inspecting the outside surface of the inspection object 1.

[Embodiment 3]

Figure 6:
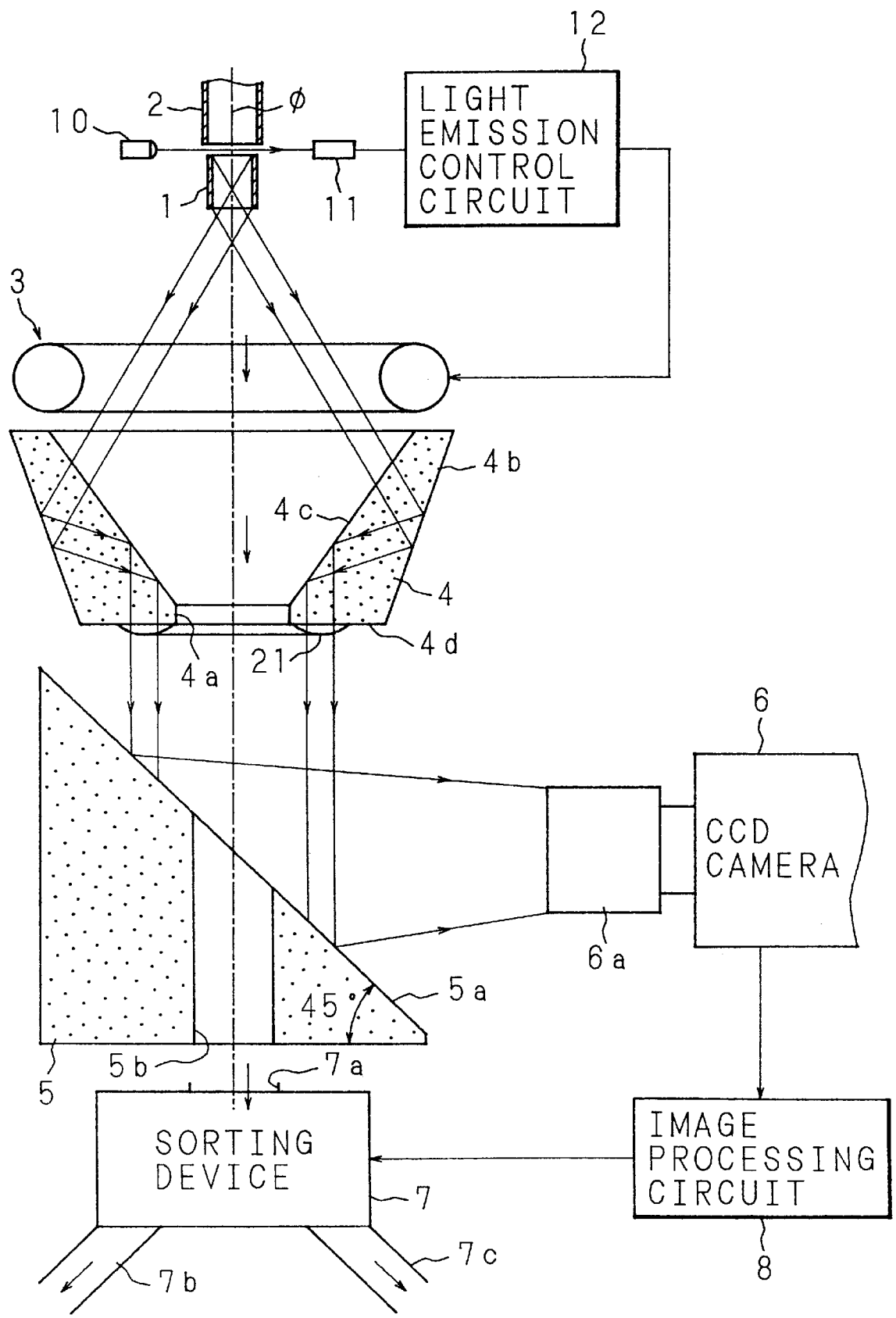
FIG. 6 is a schematic configuration diagram showing embodiment 3 of a surface inspection apparatus of the invention together with an inspection object.
Figure 7:
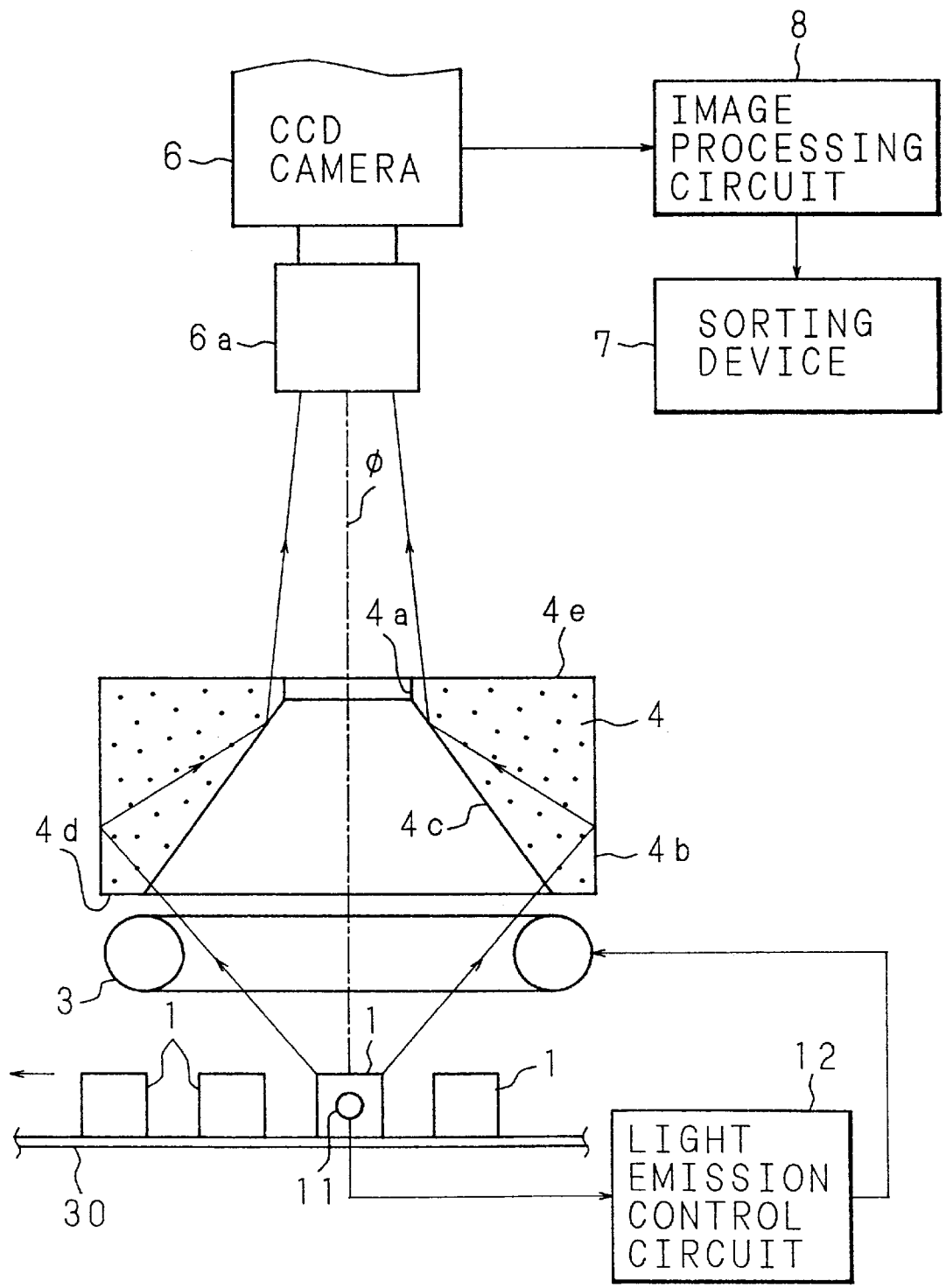
FIG. 7 is a schematic configuration diagram showing embodiment 4 of a surface inspection apparatus of the invention together with an inspection object.

Instead of the ring-shaped convex lens 20, as shown in FIG. 6, a ring-shaped convex lens 21 may be integrally formed at lower end 4d of a cone prism 4. Also, an inside surface of an inspection object 1 can be magnified and displayed same as in the case of disposing the ring-shaped convex lens 20 between the cone prism 4 and a reflector 5.

[Embodiment 4]

FIG, 7 is a schematic configuration diagram showing a surface inspection apparatus for executing the surface inspection method of the invention, together with an inspection object. A CCD camera 6 is fixed at a specified position with the photo receptor side of a lens 6a downward. At a lower position confronting the photo receptor side of the lens 6a of the CCD camera 6, an annular cone prism 4 is disposed. Inside the cone prism 4, a space of circular truncated cone is formed with a larger diameter at the lower side, and an outer circumference face 4b of the cone prism 4 is mirror-finished. A bottom 4d and a top 4e of the cone prism are orthogonal to the outer circumference face 4b, and an inner circumference face 4c forming the space of circular truncated cone is inclined at an angle of about 50° to the bottom 4d.

Beneath the cone prism 4 is disposed an annular light source 3 being a multiplicity of LEDs arranged on the circumference. Beneath the light source 3 inspection object 1 are conveyed by a conveyor 30. Each center of the lens 6a, cone prism 4 and light source 3 coincides with an optical central axis φ. At a position above the conveyor 30, coinciding with the optical central axis φ, a light emitting diode and a photo receptor transistor 11 are confronting across a spacing allowing the inspection object 1 to pass, and the receiving signal of the photo receptor transistor 11 receiving the light emitted from the light emitting diode is put into a light emission control circuit 12.

The light emission control circuit 12 allows the light source 3 to illuminate instantly when the receiving signal of the photo receptor transistor 11 is shielded by the inspection object 1. The image data issued by the CCD camera 6 is put into an image processing circuit 8. The image processing circuit 8 compares the reference image data and the image data entered from the CCD camera 6, and issues a signal for judging qualification of the inspection object 1 to feed into a sorting device 7. The sorting device 7 sorts the inspection object 1 conveyed on the conveyor 30.

A method of inspecting the surface of the inspection object by using thus constituted surface inspection apparatus is described below. The light emitting diode emits light, and the CCD camera 6 is in active state. In this state, the conveyor 30 is driven to convey the inspection objects 1. When the inspection object 1 comes to the position of the optical central axis φ, the light emitted from the light emitting diode is shielded by the inspection object 1, and the receiving signal of the photo receptor transistor 11 is off instantly. Then the light emission control circuit 12 issues a light emission control signal, this light emission control signal is supplied into the light source 3, and the light source 3 emits light instantly. As a result, the inspection object 1 positioned at the optical central axis φ is illuminated, and the light is reflected by the surface of the inspection object 1. The reflected light is put into the cone prism 4, and is reflected by the outer circumference face 4b. This reflected light is totally reflected by the inner circumference face 4c of the cone prism. The totally reflected light is emitted from the upper axial end 4e of the cone prism 4, and enters the lens 6a of the CCD camera 6.

In this way, the light reflected by the surface of the inspection object 1 is reflected by the outer circumference face 4b of the cone prism 4, and is totally reflected by the inner circumference face 4c, and thereby the outer circumference face of the inspection object 1 is developed in an annular form, and the CCD camera 6 instantly takes the outer circumference face of the inspection object 1 as shown in FIG. 2 same as mentioned above. Thus, the flaw or stain existing on the surface of the inspection object 1 can be taken. The image data issued by the CCD camera 6 and the reference image data are compared by an image processing circuit 8. If presence of flaw and stain is recognized as a result of comparison, a sorting drive signal is issued from the image processing circuit 8, and a sorting device 7 is driven, which sorts to rejects the inspection object 1 having flaw and stain out of the conveyor 30.

Figure 8:
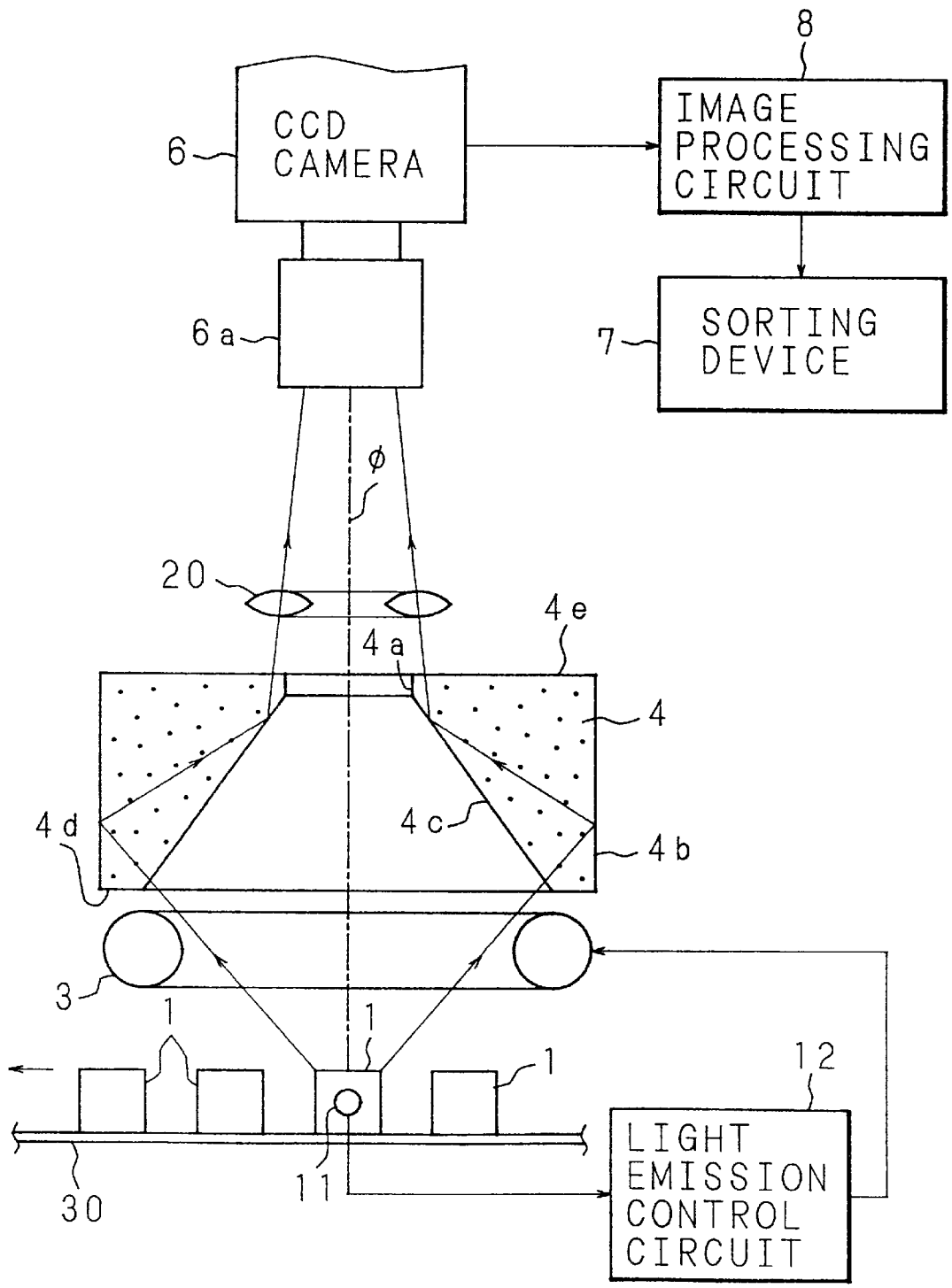
FIG. 8 is a schematic configuration diagram showing embodiment 5 of a surface inspection apparatus of the invention together with an inspection object.
Figure 9:
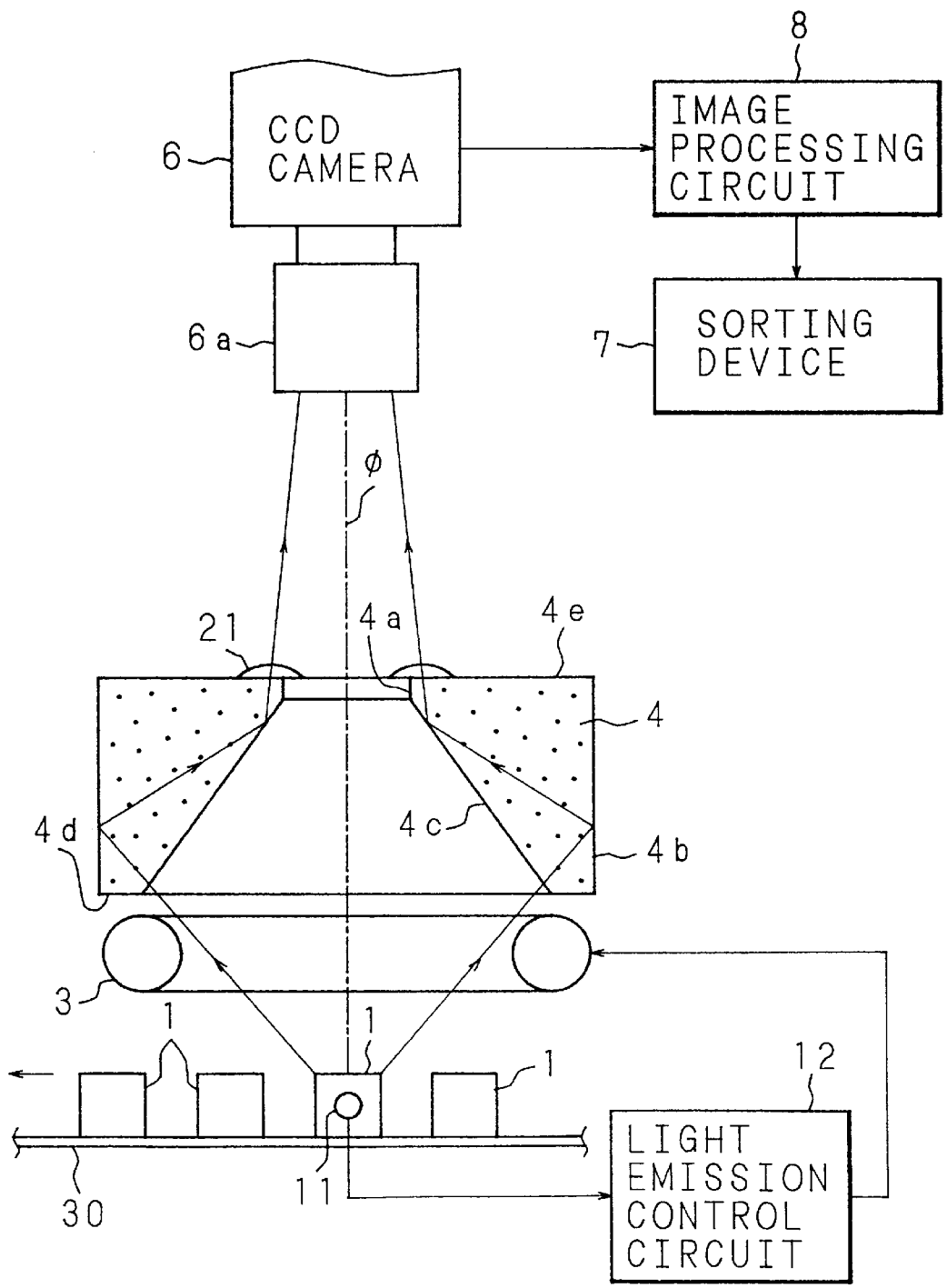
FIG. 9 is a schematic configuration diagram showing embodiment 6 of a surface inspection apparatus of the invention together with an inspection object.

Thus, without using the reflector 5 shown in FIG. 1, the same surface inspection of inspection object 1 as in the surface inspection apparatus shown in FIG. 1 can be realized. Since the reflector 5 is not used, the surface inspection apparatus can be composed compactly. Besides, as shown in FIG. 8 (embodiment 5) and FIG. 9 (embodiment 6), by disposing a ring-shaped convex lens 20 or 21 at the light exit side from the cone prism 4, the surface of the inspection object 1 can be magnified and picked-up, and the inspection precision of the inspection object 1 can be enhanced.

Figure 10:
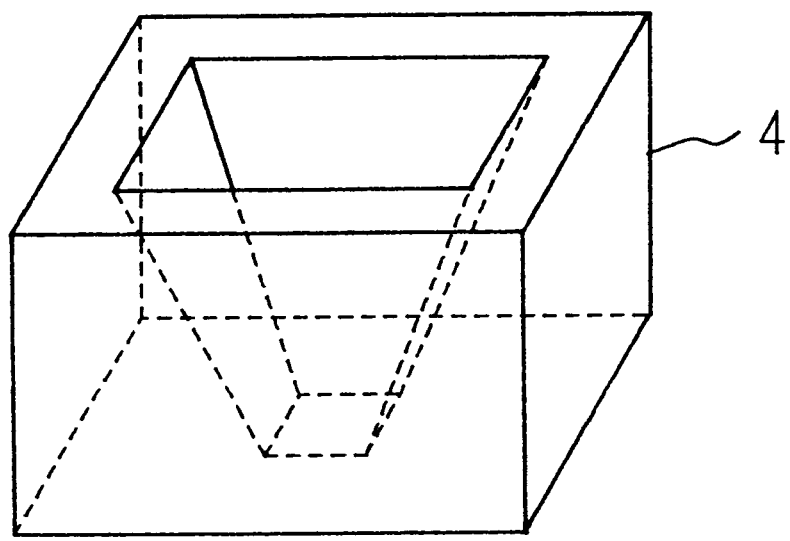
FIG. 10 is a perspective view showing a prism in a quadrangular annular form.

In the foregoing embodiments of the invention, the inspection object 1 is columnar or cylindrical, but the shape is not particularly limited and may include polyhedral column or polyhedral cylinder. In such as case, however, the annular shape of the cone prism 4 must be a polyhedral annular form suited to the polyhedral shape of the inspection object (for example, quadrangular square annular form shown in FIG. 10). The guide tube 2 for guiding the inspection object 1 is preferably shaped according to the shape of the inspection object 1.

In embodiments 1, 2 and 3 of the invention, the inspection object 1 is dropped into the sorting device 7, but when the inspection object 1 is popped out in the horizontal direction at high speed from the guide tube 2 by using, for example, an air chute, the optical central axis φ may be positioned in the lateral direction, and the cone prism 4 and reflector 5 can be disposed in the lateral direction. In this case same as in the case of disposition in the vertical direction, the surface can be inspected similarly and same effects are obtained.

Moreover, in embodiments 1 and 2, at an upper position of the prism, the reflected light from the inspection object is put into the prism, and the light emitted from the prism is projected onto the reflector provided beneath the prism. Same effects are obtained by inverting the prism upside down to enter the reflected light from the inspection object when the inspection object is positioned beneath the prism into the prism, and project the light emitted from the prism onto the reflector provided above the prism.

Still more, instead of instant lighting of the light source 3, the light source 3 may emit light continuously, and the same effects are obtained by taking with the CCD camera 6 instantly when the inspection object 1 gets into the picking-up field of the CCD camera 6. Or, the inspection object 1 is not limited to small objects, but drums and others may be inspected similarly.

As described herein, according to the invention, the surface can be inspected instantly without rotating the inspection object, and the surface of the inspection object can be inspected without causing flaw or stain. Hence, it does not require mechanism for supporting the inspecting object and rotating about the axis, and the surface inspection method and surface inspection apparatus capable of inspecting the surface of inspection object at high speed and at low cost are obtained. Besides, by disposing a ring-shaped lens at the light exit side of the annular prism, the surface of the inspection object can be magnified and displayed. Therefore, the surface inspection method, surface inspection apparatus, and prism used in surface inspection of an outstandingly high inspection efficiency can be presented, which contributes greatly to the industries.

As this invention may be embodied in several forms without departing from the spirit of essential characteristics thereof, the present embodiments are therefore illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

I claim:

1. A method for optically inspecting the surface of an inspection object, said method making use of an annular prism having a conical bore defining an interior space comprising the steps of:
   providing an interior wall within the annular prism which is constructed to reflect light incident thereon internally within the prism;
   admitting light from the inspection object into the interior space of the annular prism so that it enters the prism and reflects off of the interior wall and is emitted from within the prism;
   picking-up light emitted from the prism to form a picked-up image; and
   inspecting the surface of the inspection object by examining the picked-up image.

2. An apparatus for inspecting the surface of an inspection object optically, comprising:
   an annular prism having a conical bore bounded by an interior surface defining an interior space, the interior surface being constructed and positioned to receive light emitted from the inspection object, said prism further having an internal wall constructed to reflect light incident thereon internally within the prism so as to be emitted therefrom; and
   picking-up means positioned for picking up light originating from the inspection object and emitted from the prism.

3. An apparatus in accordance with claim 2, further comprising, reflector having a penetration hole allowing the inspection object to pass through, for reflecting and projecting the light emitted form the prism, wherein said picking-up means picks up the image projected on the reflector.

4. An apparatus as in claim 3, wherein said prism and said reflector are disposed in linear alignment.

5. An apparatus of claim 3, further comprising:
   a light source for emitting light to the surface of the inspection object; and
   light emission control means for controlling emission of said light source when the inspection object gets into the picking-up field of the picking-up means,
   wherein said prism includes:
      a space a circular truncated cone of which one side is larger in diameter than the other side;
      a circumference face for reflecting the light entering from the larger diameter side of the space; and
      an axial direction end surface at the smaller diameter of the space, for emitting the reflected light, and
   said picking-up means picks up the image of the outside or inside surface of the inspection object displayed on the reflector when the light source emits light.

6. An apparatus of claim 5, further comprising a ring-shaped lens at the light exit side of the prism.

7. An apparatus of claim 2, wherein said prism is composed of a columnar light permeable material, having a circular truncated cone shape interior space which is opened at both axial ends.

8. An apparatus of claim 7, wherein said prism includes:
   a circumference face for reflecting the light entering from the larger diameter side of the space; and
   an axial end face at the smaller diameter side of the space, for emitting the reflected light.

9. An apparatus for inspecting the surface of an inspection object optically, comprising:
   an annular prism in which the light from the inspection object; is entered; and
   picking-up means for picking up the light emitted from the prism; and
   a ring-shaped lens at the light exit side of the prism.

10. An apparatus for inspecting the surface of an inspection object optically, comprising:
    an annular prism having a conical bore bounded by an interior surface defining an interior space, the interior surface being constructed and positioned to receive light emitted from the inspection object; and
    picking-up means positioned for picking up light originating from the inspection object and emitted from the prism;

a reflector having a penetration hole allowing the inspection object to pass through, for reflecting and projecting the light emitted form the prism, wherein said picking-up means picks up the image projected on the reflector; and a ring-shaped lens at a light exit side of the prism.

11. An apparatus for inspecting the surface of an inspection object optically, comprising:

an annular prism having a conical bore bounded by an interior surface defining an interior space, the interior surface being constructed and positioned to receive light emitted from the inspection object; and picking-up means positioned for picking up light originating from the inspection object and emitted from the prism;

a reflector having a penetration hole allowing the inspection object to pass through, for reflecting and projecting the light emitted form the prism, wherein said picking-up means picks up the image projected on the reflector;

said prism and said reflector being disposed in linear alignment; and a ring-shaped lens at a light exit side of the prism.

12. A prism composed of a columnar light permeable material, having an interior space having a circular truncated cone shape opened at both axis ends, the prism having a bounding surface for the interior space which is constructed to reflect light incident thereon which is directed towards the inferior space, while transmitting light incident thereon from within the interior space.

13. A prism of claim 10, wherein an outer circumferential face thereof is orthogonal to said axial end side.

14. A prism comprised of a columnar light permeable material, having an interior space having a truncated pyramid shape opened at both axial ends, the prism having a bounding surface for the interior space which is constructed to reflect light incident thereon which is directed towards the interior space, while transmitting light incident thereon from within the interior space.

15. An apparatus for inspecting the surface of an inspection object optically, comprising:

an annular prism having a conical bore bounded by an interior surface defining an interior space, the interior surface being constructed and positioned to receive light emitted from the inspection object;

picking-up means positioned for picking up light originating from the inspection object and emitted from the prism; and said prism is composed of a columnar light permeable material, having a truncated pyramid shape interior space which is opened at both axial ends.

16. An apparatus of claim 15, wherein said prism includes:

a circumference face for reflecting the light entering from the larger diameter side of the space; and an axial end face at the smaller diameter side of the space, for emitting the reflected light.

* * * * *